United States Patent
Kaps et al.

(10) Patent No.: US 12,035,429 B2
(45) Date of Patent: Jul. 9, 2024

(54) NARROWBAND ULTRAVIOLET SAUNA

(71) Applicant: Sauna Works Inc., Berkeley, CA (US)

(72) Inventors: Andrew Kaps, San Francisco, CA (US); Raleigh Duncan, Berkeley, CA (US)

(73) Assignee: SAUNA WORKS INC., Berkeley, CA (US)

( * ) Notice: Subject to any disclaimer, the term of this patent is extended or adjusted under 35 U.S.C. 154(b) by 0 days.

(21) Appl. No.: 15/832,646

(22) Filed: Dec. 5, 2017

(65) Prior Publication Data

US 2019/0167519 A1 Jun. 6, 2019

(51) Int. Cl.
*H05B 45/10* (2020.01)
*A61H 33/06* (2006.01)
(Continued)

(52) U.S. Cl.
CPC ........... *H05B 45/10* (2020.01); *A61H 33/063* (2013.01); *A61H 33/066* (2013.01);
(Continued)

(58) Field of Classification Search
CPC .................. A61H 33/06; A61H 33/063; A61H 2201/0221; A61H 2003/061; A61N 5/0616; A61N 2005/0636; A61N 2005/0661
(Continued)

(56) References Cited

U.S. PATENT DOCUMENTS 2,590,336 A * 3/1952 Mast ....................... F24H 3/002
  392/374
3,394,412 A * 7/1968 Olssen ................... A61H 33/06
  4/532
(Continued)

FOREIGN PATENT DOCUMENTS

CN    1217946 A  † 6/1999
CN   102179009 A  † 9/2011
(Continued)

OTHER PUBLICATIONS

Adam Reich and Karolina Mędrek, Effects of Narrow Band UVB (311 nm) Irradiation on Epidermal Cells, Apr. 2013, International Journal of Molecular Science. (Year: 2013).*
(Continued)

*Primary Examiner* — Erin Deery
(74) *Attorney, Agent, or Firm* — Kwan & Olynick LLP (57) ABSTRACT

Systems, devices, and methods are disclosed herein for ultraviolet saunas. Systems include a plurality of walls of an enclosure, the enclosure being a sauna enclosure configured to accommodate a user. The systems further include a plurality of heating elements coupled to the plurality of walls, a plurality of emissive elements configured to generate ultraviolet (UV) light, and a controller coupled to the plurality of heating elements and the plurality of emissive elements. The controller includes one or more processors configured to generate activation properties for each of the plurality of heating elements and the plurality of emissive
(Continued)

elements, activate at least one of the plurality of heating elements based on the plurality of activation properties, and activate the at least one emissive element based on the plurality of activation properties.

13 Claims, 8 Drawing Sheets

(51) Int. Cl.
    *A61N 5/06*         (2006.01)
    *H05B 3/00*         (2006.01)
    *H05B 47/19*       (2020.01)

(52) U.S. Cl.
    CPC ......... *A61H 33/067* (2013.01); *A61N 5/0616* (2013.01); *A61N 5/0625* (2013.01); *H05B 3/0085* (2013.01); *H05B 47/19* (2020.01); *A61H 2033/061* (2013.01); *A61H 2201/0207* (2013.01); *A61H 2201/0221* (2013.01); *A61H 2201/10* (2013.01); *A61H 2201/501* (2013.01); *A61H 2201/5025* (2013.01); *A61H 2201/5041* (2013.01); *A61H 2201/5043* (2013.01); *A61H 2201/5058* (2013.01); *A61H 2201/5097* (2013.01); *A61H 2230/655* (2013.01); *A61H 2230/805* (2013.01); *A61H 2230/825* (2013.01); *A61N 2005/0636* (2013.01); *A61N 2005/064* (2013.01); *A61N 2005/0661* (2013.01)

(58) Field of Classification Search
    USPC .................................. 601/15, 16; 607/91, 94
    See application file for complete search history.

(56) References Cited

U.S. PATENT DOCUMENTS

| | | | |
|---|---|---|---|
| 3,564,201 A * | 2/1971 | Jones | A61H 33/06 392/372 |
| 7,108,712 B2 * | 9/2006 | Barghelame | A61H 33/06 607/88 |
| 9,744,098 B2 * | 8/2017 | O'Keeffe | A61H 33/06 |
| 10,226,641 B2 † | 3/2019 | Moffat | |
| 2013/0172963 A1 * | 7/2013 | Moffat | A61N 5/0616 607/94 |
| 2014/0283294 A1 | 9/2014 | O'Keefe et al. | |
| 2016/0114186 A1 * | 4/2016 | Dobrinsky | A61B 5/0071 607/94 |
| 2016/0325114 A1 † | 11/2016 | Wagenaar Cacciola | |

FOREIGN PATENT DOCUMENTS

| | | | |
|---|---|---|---|
| JP | 3011676 U † | 5/1995 | |
| JP | 2003275274 A * | 9/2003 | |
| WO | 2019113108 A1 | 6/2019 | |

OTHER PUBLICATIONS

UV Light, Stanford Solar Center, 2015. (Year: 2015).*
"Int'l Application Serial No. PCT/US18/63905, Int'l Search Report and Written Opinion mailed Mar. 14, 2019", 8 pgs.

\* cited by examiner
† cited by third party

NARROWBAND ULTRAVIOLET SAUNA

TECHNICAL FIELD

The present disclosure relates generally to saunas, and more specifically to heating elements, emissive elements, and controls included in saunas.

DESCRIPTION OF RELATED ART

Saunas may be rooms or enclosed areas in which heat may be used to make users of the saunas perspire. Accordingly, an enclosed area of a sauna may be heated such that the temperature inside the sauna is elevated relative to an exterior temperature. While saunas are able to generate and retain heat, saunas remain limited in their ability to address various therapeutic needs of the sauna users. For example, saunas remain limited in their ability to effectively and efficiently address multiple therapeutic needs at the same time, and in a manner that is configured for the therapeutic needs of a particular user.

SUMMARY

Systems include a plurality of walls of an enclosure, the enclosure being a sauna enclosure configured to accommodate a user. The systems further include a plurality of heating elements coupled to the plurality of walls, a plurality of emissive elements configured to generate ultraviolet (UV) light, and a controller coupled to the plurality of heating elements and the plurality of emissive elements. The controller includes one or more processors configured to generate activation properties for each of the plurality of heating elements and the plurality of emissive elements, activate at least one of the plurality of heating elements based on the plurality of activation properties, and activate the at least one emissive element based on the plurality of activation properties.

In some embodiments, the plurality of emissive elements is configured to emit narrowband UV wavelengths. In various embodiments, the activation properties identify a duration and intensity of activation for each of the plurality of heating elements and each of the plurality of emissive elements. According to some embodiments, the activation properties are determined based, at least in part, on a plurality of characteristics of the user. In some embodiments, the characteristics of the user include one or more identified health conditions of the user, and one or more identified nutritional requirements of the user. In various embodiments, the duration and intensity of the activation of at least one of the plurality of emissive elements is determined based on the one or more identified nutritional requirements of the user. According to some embodiments, the plurality of heating elements includes a first plurality of heating elements configured to provide heat to a first portion of the user, and a second plurality of heating elements configured to provide heat to a second portion of the user.

In some embodiments, the plurality of heating elements includes infrared heating elements configured to generate at least one of near infrared, mid infrared, and far infrared wavelengths. Systems also include a door, wherein the at least one emissive element is mounted on the door. In various embodiments, systems also include a seat configured to enable the user to sit in a seated position within the enclosure, wherein the seat includes an additional plurality of heating elements, and wherein the controller is further configured to control operation of the additional plurality of heating elements.

Also disclosed herein are systems that may include a plurality of walls of an enclosure, the enclosure being a sauna enclosure configured to accommodate a user. The systems further include a plurality of heating elements coupled to the plurality of walls, the plurality of heating elements configured to generate heat. The systems also include at least one emissive element configured to generate ultraviolet (UV) light, and a controller configured to control operation of the plurality of heating elements and the at least one emissive element, the controller being configured to generate activation properties for each of the plurality of heating elements and the at least one emissive element.

In some embodiments, the plurality of heating elements includes a first plurality of heating elements configured to provide heat to a first portion of the user, and a second plurality of heating elements configured to provide heat to a second portion of the user. In various embodiments, the plurality of heating elements includes infrared heating elements configured to generate at least one of near infrared, mid infrared, and far infrared wavelengths. According to some embodiments, the at least one emissive element is configured to emit narrowband UV wavelengths, and wherein the at least one emissive element is mounted on the door. In some embodiments, the activation properties identify a duration and intensity of activation for each of the plurality of heating elements and the at least one emissive element, and the activation properties are determined based, at least in part, on a plurality of characteristics of the user. In various embodiments, systems also include a seat configured to enable the user to sit in a seated position within the enclosure, wherein the seat includes an additional plurality of heating elements, and wherein the controller is further configured to control operation of the additional plurality of heating elements.

Further disclosed herein are methods that may include generating, using a processor of a controller, a plurality of activation properties associated with a plurality of heating elements and at least one emissive element, the plurality of heating elements and the at least one emissive element being included in a sauna enclosure, activating at least one of the plurality of heating elements in accordance with a first duration and intensity determined based on the plurality of activation properties, and activating the at least one emissive element in accordance with a second duration and intensity determined based on the plurality of activation properties.

In some embodiments, the plurality of heating elements generates at least one of near infrared, mid infrared, and far infrared wavelengths responsive to being activated, and the at least one emissive element emits narrowband UV wavelengths responsive to being activated. In various embodiments, the activation properties are determined based, at least in part, on a plurality of characteristics of the user, and the characteristics of the user include one or more identified health conditions of the user, and one or more identified nutritional requirements of the user. According to some embodiments, the duration and intensity of the activation of the at least one emissive element is determined based on the one or more identified nutritional requirements of the user.

BRIEF DESCRIPTION OF THE DRAWINGS

The disclosure may best be understood by reference to the following description taken in conjunction with the accompanying drawings, which illustrate particular embodiments.

DESCRIPTION OF EXAMPLE EMBODIMENTS

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

For example, the techniques of the present invention will be described in the context of saunas, and heating and emissive elements associated with such saunas. However, it should be noted that the techniques of the present invention apply to a wide variety of different environments and enclosures. In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise. For example, a system uses a processor in a variety of contexts. However, it will be appreciated that a system can use multiple processors while remaining within the scope of the present invention unless otherwise noted. Furthermore, the techniques and mechanisms of the present invention will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of components may reside between the processor and memory. Consequently, a connection does not necessarily mean a direct, unimpeded connection unless otherwise noted.

Overview

Techniques and mechanisms described herein provide for the configuration of saunas to implement a combination of multiple heating elements and emissive elements. In some embodiments, such saunas are configured to operate such combinations of heating elements and emissive elements to address a variety of therapeutic needs of a user. As will be discussed in greater detail below, various embodiments disclosed herein include various heating elements that emit infrared wavelengths, as well as various emissive elements that emit narrowband ultraviolet (UV) wavelengths. Moreover, the operation of the heating elements and emissive elements may be implemented in conjunction to address multiple therapeutic issues simultaneously, and in a manner that is specifically configured for each particular user.

Example Embodiments

Figure 1:
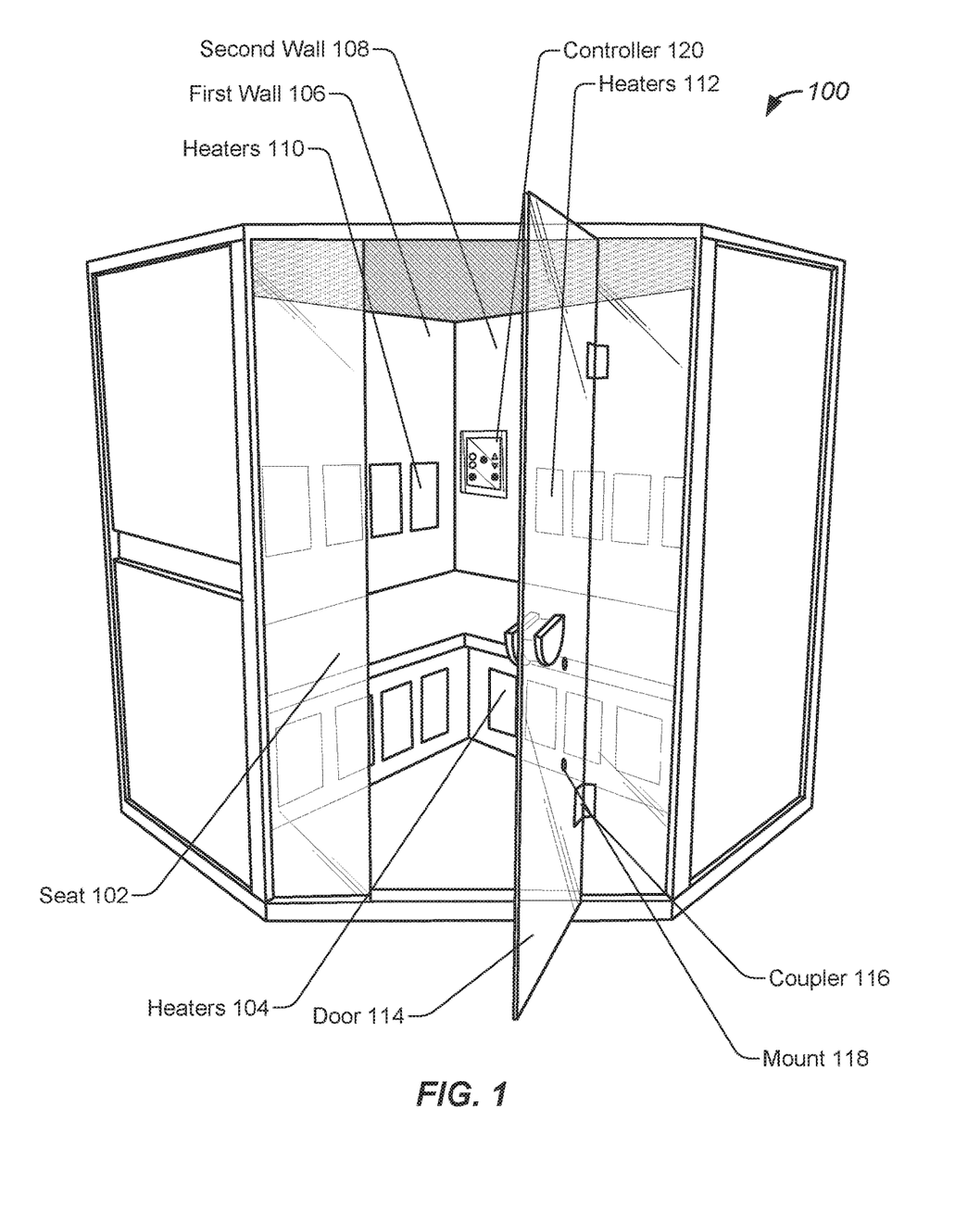
FIG. 1 illustrates an example of a sauna, configured in accordance with some embodiments.

FIG. 1 illustrates an example of a sauna, configured in accordance with some embodiments. As will be discussed in greater detail below, sauna 100 may be a climate and humidity controlled enclosure which includes various heating elements configured to provide heat to one or more users that may be included inside the enclosure of sauna 100. In various embodiments, the heat is provided in a therapeutic manner that is configured to address and/or alleviate one or more conditions or ailments of users of the sauna. As will be discussed in greater detail below, the heating elements may be many different types of heating elements which are configured to operation in combination to implement a therapeutic treatment.

As discussed above, sauna 100 may be an enclosure that is configured to accommodate one or more users in a standing and/or sitting position. Sauna 100 includes seat 102, which may be a bench. In various embodiments, seat 102 includes a plurality of heaters, such as heaters 104. Moreover, walls of sauna 100, such as first wall 106 and second wall 108, may each include pluralities of heaters as well, such as heaters 110 and heaters 112. In various embodiments, heaters 104, heaters 110, and heaters 112 may all include the same type of heating element, or may include different types of heating elements. For example, the heating elements may be infrared heating elements configured to emit one or more of near infrared, mid infrared, or far infrared wavelengths. Accordingly, each of the heating elements may be configured to emit a specific infrared wavelength, such as just far infrared wavelengths, or the entire band of near infrared, mid infrared, and far infrared wavelengths. In one specific example, the heating elements may be carbon fiber impregnated heating elements that are configured to have reduced electromagnetic field (EMF) emissions. In some embodiments, such EMF emissions may be about 2.5 milligauss.

In various embodiments, heating elements may be configured to be variable. More specifically, a wavelength emitted by a heating element may be varied from one wavelength regime to another. For example, a heating element may be configured to be varied between near infrared, mid infrared, or far infrared wavelengths. In some embodiments, such variation may be implemented by modulating a surface temperature of the heating element. Accordingly, a surface temperature of a heating element may be increased to emit shorter wavelengths, and a surface temperature may be decreased to emit longer wavelengths. Such wavelength modulation may be implemented in a manner consistent with activation properties determined by controller 120 discussed in greater detail below. In this way, particular heating elements may be modulated to implement various different wavelength regimes in accordance with a comprehensive heating treatment determined by controller 120.

Sauna 100 may also include door 114 which may be coupled to the rest of the enclosure of sauna 100 via one or more couplers, such as coupler 116. In some embodiments, coupler 116 may be a hinge that is configured to provide free rotation of door 114 while supporting an additional emissive element mounted to door 114, and while also not interfering with the operation of the additional heating element. In some embodiments, door 114 includes mount 118 which is configured to provide an attachment point for the additional emissive element, as will be discussed in greater detail below with reference to at least FIG. 3 and FIG. 4. In some embodiments, the position and height of mount 118 is configured to be at torso-height relative to a user, as will be discussed in greater detail below with reference to FIG. 3. Accordingly, the additional emissive element may be positioned and oriented to improve the emission of one or more wavelengths to a user of sauna 100.

Sauna 100 may further include controller 120 which may include one or more processing components, as discussed in greater detail with reference to FIG. 7, which are configured to control the operation of heating elements, such as heaters 104, heaters 110, and heaters 112. Moreover, controller 120 may be configured to control the operation of the additional emissive element is removably coupled with door 114. As will be discussed in greater detail below, controller 120 may control the operation of the heaters and emissive elements independently and/or in conjunction to implement one or more comprehensive heating sessions that may be specifically configured for a particular user, and that is configured based on one or more characteristics of the user. In various embodiments, controller 120 may be implemented as a variable switch, dial, or other suitable controller. For example, controller 120 may include one or more mechanical or analog components configured to control the operation of heating elements and emissive elements included in sauna 100.

Figure 2:
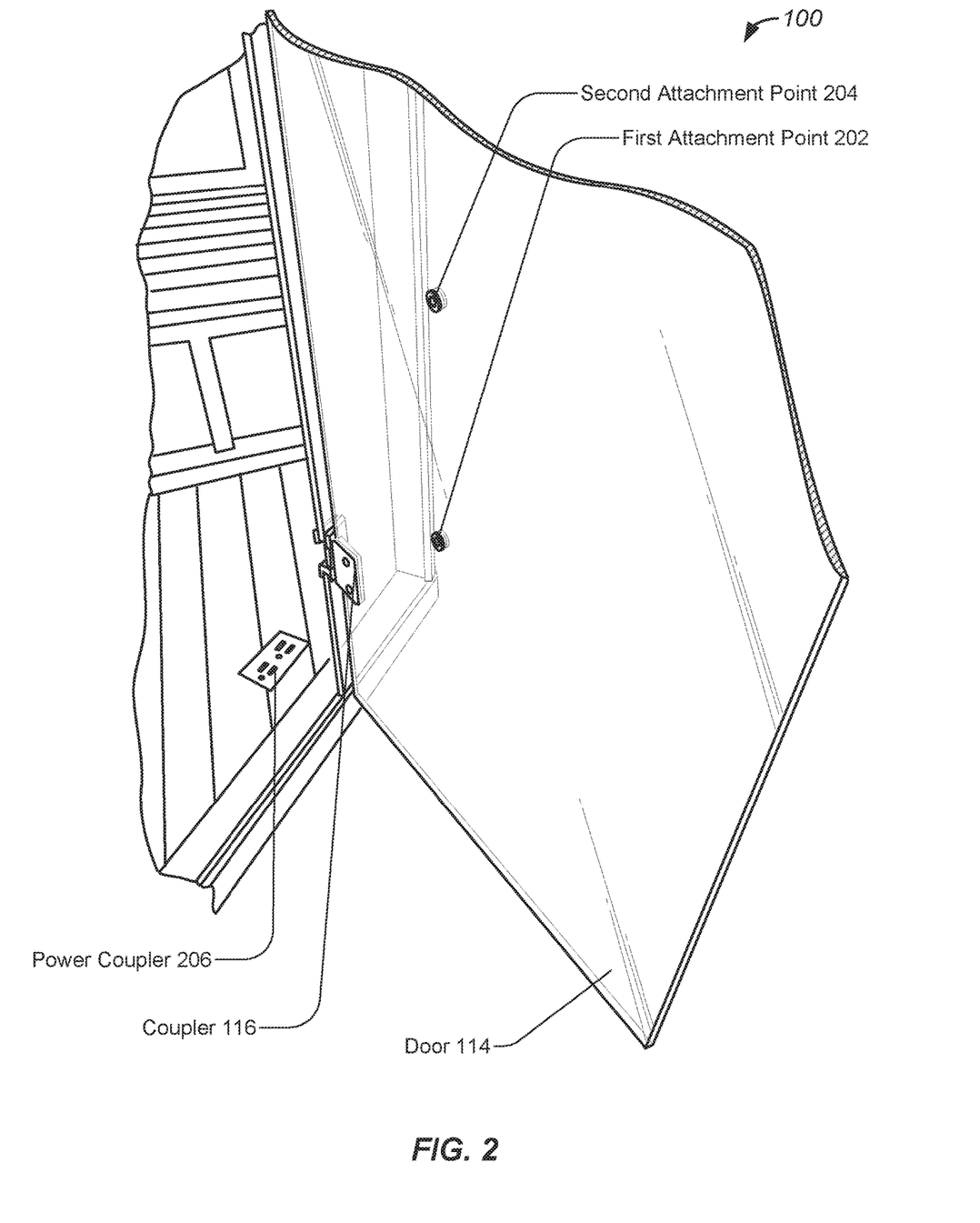
FIG. 2 illustrates an example of a portion of a sauna, configured in accordance with some embodiments.

FIG. 2 illustrates an example of a portion of a sauna, configured in accordance with some embodiments. As discussed above, a sauna, such as sauna 100, may include a door, such as door 114, which may be coupled to an enclosure of a sauna via a coupler, such as coupler 116. Furthermore, door 114 may include mount 118, which may include one or more attachment points, such as first attachment point 202 and second attachment point 204. As will be discussed in greater detail below with reference to FIG. 3, such attachment points may be configured to be coupled with corresponding attachment points on an emissive element. Moreover, sauna 100 may also include power coupler 206 which may be configured to couple with the mounted emissive element, and may be further configured to provide power to the emissive element. As will be discussed in greater detail below, the operation of power coupler 206 may be controlled by controller 120. In one example, controller 120 is configured to enable and/or disable power coupler 206 as well as control the operation of the emissive element coupled with power coupler 206.

Figure 3:
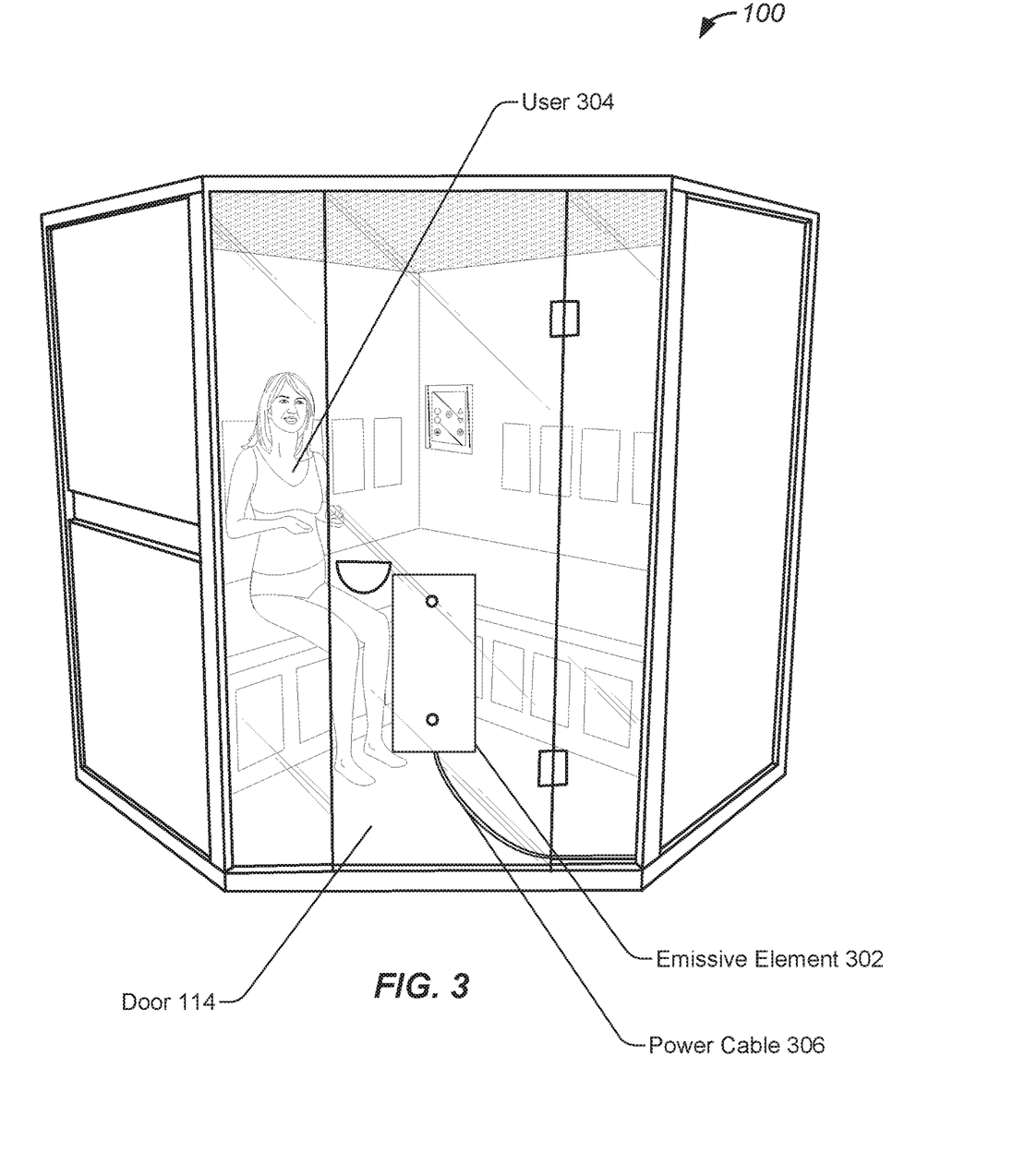
FIG. 3 illustrates another example of a sauna, configured in accordance with some embodiments.

FIG. 3 illustrates another example of a sauna, configured in accordance with some embodiments. As discussed above, a sauna, such as sauna 100, may include a door, such as door 114 which may be coupled with an additional emissive element, such as emissive element 302 which may include a power cable, such as power cable 306. As shown in FIG. 3, a user, such as user 302 may be positioned inside sauna 100, and may be seated facing emissive element 302. As similarly discussed above, the position of emissive element 302 may be configured based on one or more emission characteristics associated with the user. For example, emissive element 302 may be positioned at a height determined based on the user's torso height while seated. Moreover, the distance and angle between the user and emissive element 302 may also be configured based on one or more emission characteristics, such as a target absorption rate of wavelengths emitted by emissive element 302, as will be discussed in greater detail below. While FIG. 3 illustrates one example of a configuration of an emissive element, various other embodiments and configurations are contemplated herein. For example, sauna 100 may include multiple emissive elements. Moreover, emissive element 302, or an additional emissive element, may be mounted on a ceiling of sauna 100, or other surface.

Figure 4:
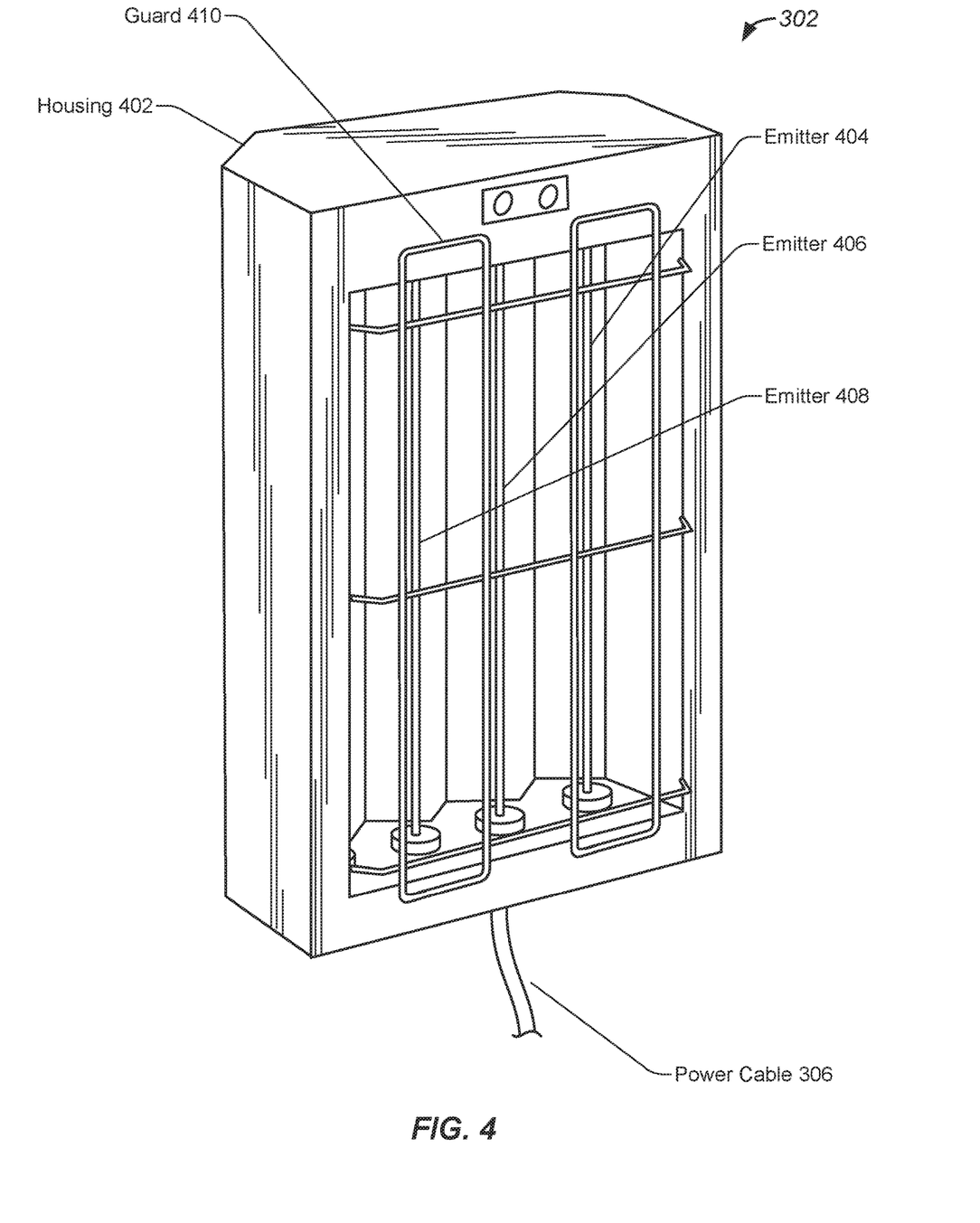
FIG. 4 illustrates an example of an emissive element, configured in accordance with some embodiments.

FIG. 4 illustrates an example of an emissive element, configured in accordance with some embodiments. As discussed above, emissive element 302 may include power cable 306, which may be configured to provide power coupling and operational coupling with other components of sauna 100, such as controller 120. In various embodiments, an emissive element, such as emissive element 302, may be configured to emit one or more wavelengths that is configured to provide one or more therapeutic treatments for a user. In one example, emissive element 302 is configured to emit ultraviolet (UV) radiation. More specifically, emissive element 302 may be configured to emit narrowband UV radiation. In some embodiments, the wavelengths emitted by emissive element 302 may be between about 295 and 320 nanometers. Such wavelengths may promote the generation of vitamin D by the user.

Accordingly, in some embodiments, emissive element 320 includes a housing, such as housing 402 which is configured to provide an enclosure for one or more components of emissive element 302, as well as structural support for one or more components of emissive element 302. In various embodiments, emissive element 302 further includes one or more emitters, such as emitter 404. In some embodiments, emitters, such as emitter 404, are configured to emit wavelengths that promote vitamin D generation in a user. In this way, the wavelengths emitted by emitters of emissive element 302 may be combined with other wavelengths emitted by other elements, such as the previously discussed heating elements, to provide the user with a comprehensive therapeutic treatment that addresses several therapeutic characteristics of the user. In various embodiments, emitter 404 may be a narrowband UV lamp. Moreover, other emitters, such as emitter 406 and emitter 408, may also be narrowband UV lamps, or emissive elements configured to emit one or more other wavelength bands. In some embodiments, emissive element 302 may include various other types of emitters, such as light emitting diodes (LEDs) configured to emit UV wavelengths. In this way, emissive element 302 may be configured to implement one or more of various different emissive modalities. In various embodiments, emissive element 302 further includes guard 410 which is configured to provide protection for the emitters, and prevent contact between the emitters and other objects.

Figure 5:
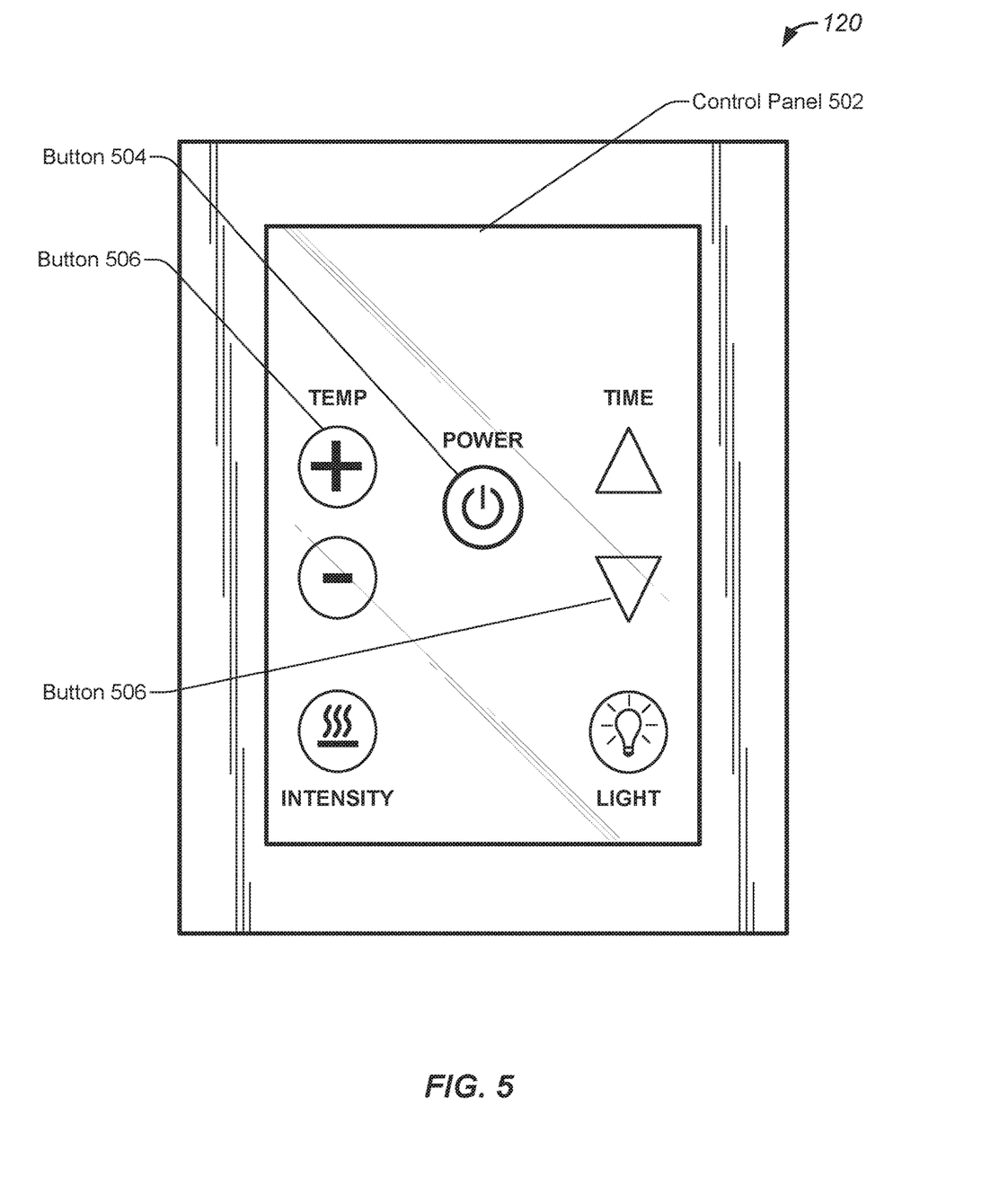
FIG. 5 illustrates an example of a controller, configured in accordance with some embodiments.

FIG. 5 illustrates an example of a controller, configured in accordance with some embodiments. As discussed above, a controller, such as controller 120, may be configured to control the operation of various heating elements and emissive elements included in a sauna. Moreover, controller 120 may be configured to control such operations to implement one or more therapeutic treatments to address one or more therapeutic characteristics of a user. In one example, control of heating elements, which may be characterized by intensity and duration of emission, may be determined based on characteristics of a user, such as the presence of muscle and joint pain as well as skin conditions such as psoriasis. Such characteristics may have been previously indicated by a user, or retrieved from a user profile. Moreover, control of emissive elements may be determined based on additional attributes of the user, such as a gender, age, and size, as may have also been previously indicated by a user, or retrieved from a user profile. Accordingly, controller 120 may operate the heating elements and the emissive elements in conjunction to address the therapeutic conditions identified by the user, as well as the vitamin D needs of the user.

In some embodiments, controller 120 includes control panel 502 which is configured to receive one or more inputs from a user, and is further configured display various information to the user. In various embodiments, control panel 502 includes various buttons. For example, control panel 502 includes buttons 504 which may be configured to receive a manual input for power on/off operation. In various embodiments, such on/off control may be implemented based on one or more other inputs, such as those provided by a sensor. Control panel 502 may further include buttons 506 which may be configured to receive a manual input for temperature settings. In various embodiments, control panel 502 also includes buttons 508 which may be configured to receive a manual input for time settings. Additional details regarding the operation of heating elements and emissive elements as controlled by controller 120 are discussed in greater detail below with reference to FIG. 6 and FIG. 7.

Figure 6:
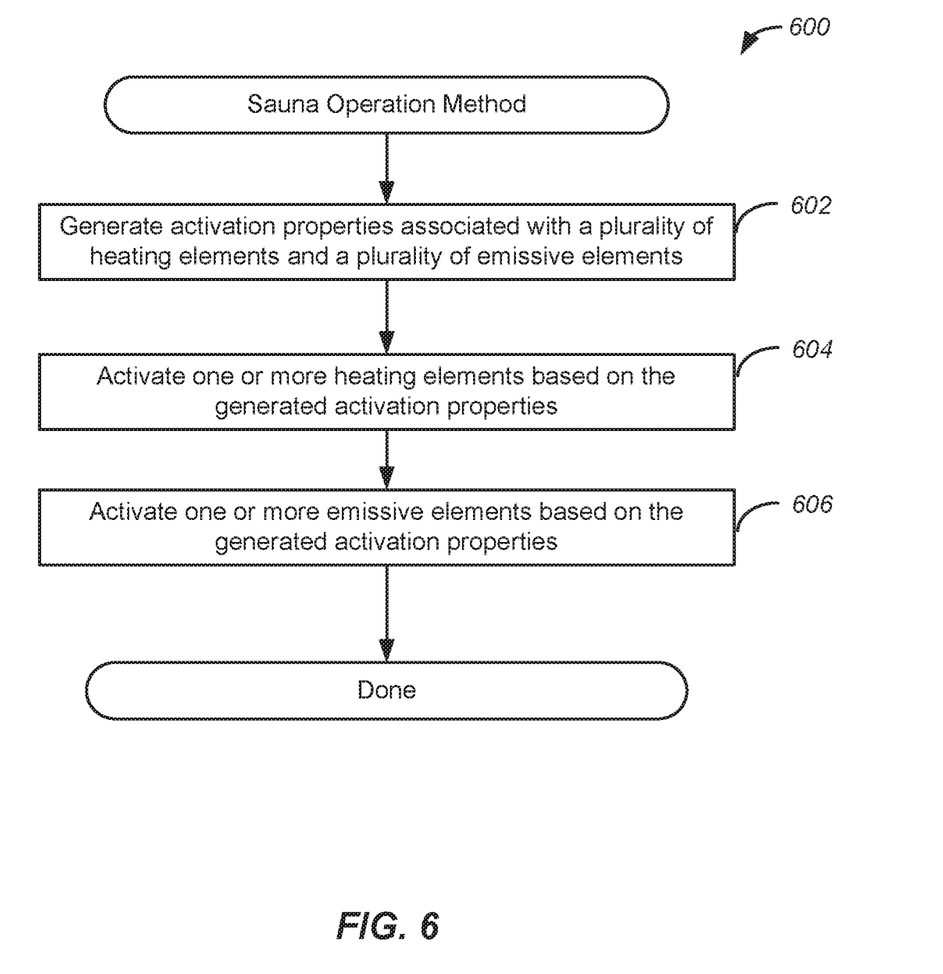
FIG. 6 illustrates a flow chart of an example of a method for controlling a sauna, implemented in accordance with some embodiments.

FIG. 6 illustrates a flow chart of an example of a method for controlling a sauna, implemented in accordance with some embodiments. As discussed above, one or more characteristics or criteria may be used by a controller, such as controller 120, to control an operation of various heating elements and emissive elements included in the sauna. As will be discussed in greater detail below, the control of the heating elements and emissive elements may be implemented based on user characteristics and features retrieved from a variety of sources, as well as a combination of sources. Moreover, the control of the heating elements and emissive elements may be implemented in combination to efficiently and effectively address multiple therapeutic issues simultaneously.

Accordingly, method 600 may commence with operation 602 during which activation properties associated with heating elements and emissive elements may be generated. In various embodiments, the activation properties may determine times/durations and intensities of the activation and deactivation of heating elements and emissive elements. Accordingly, such activation properties characterize when each individual heating element and emissive element is active and inactive over a given period of time, which may be a particular therapeutic session. As will be discussed in greater detail below, the activation properties may be determined based on various characteristics of the user, as well as one or more identified conditions associated with the user.

Method 600 may proceed to operation 604 during which one or more heating elements is activated based on the activation properties. Accordingly, the controller may activate one or more heating elements based on the previously generated activation properties. As similarly discussed above, activation may be for a designated period of time at a designated intensity. In this way, a particular amount of infrared radiation may be provided to the user in a manner that is specifically configured based on the user's needs.

Method 600 may proceed to operation 606 during which one or more emissive elements is activated based on the activation properties. Thus, according to various embodiments, the controller may activate one or more emissive elements based on the previously generated activation properties. As similarly discussed above, activation may be for a designated period of time at a designated intensity. In this way, a particular amount of narrowband UV radiation may be provided to the user in a manner that is specifically configured based on the user's needs.

Figure 7:
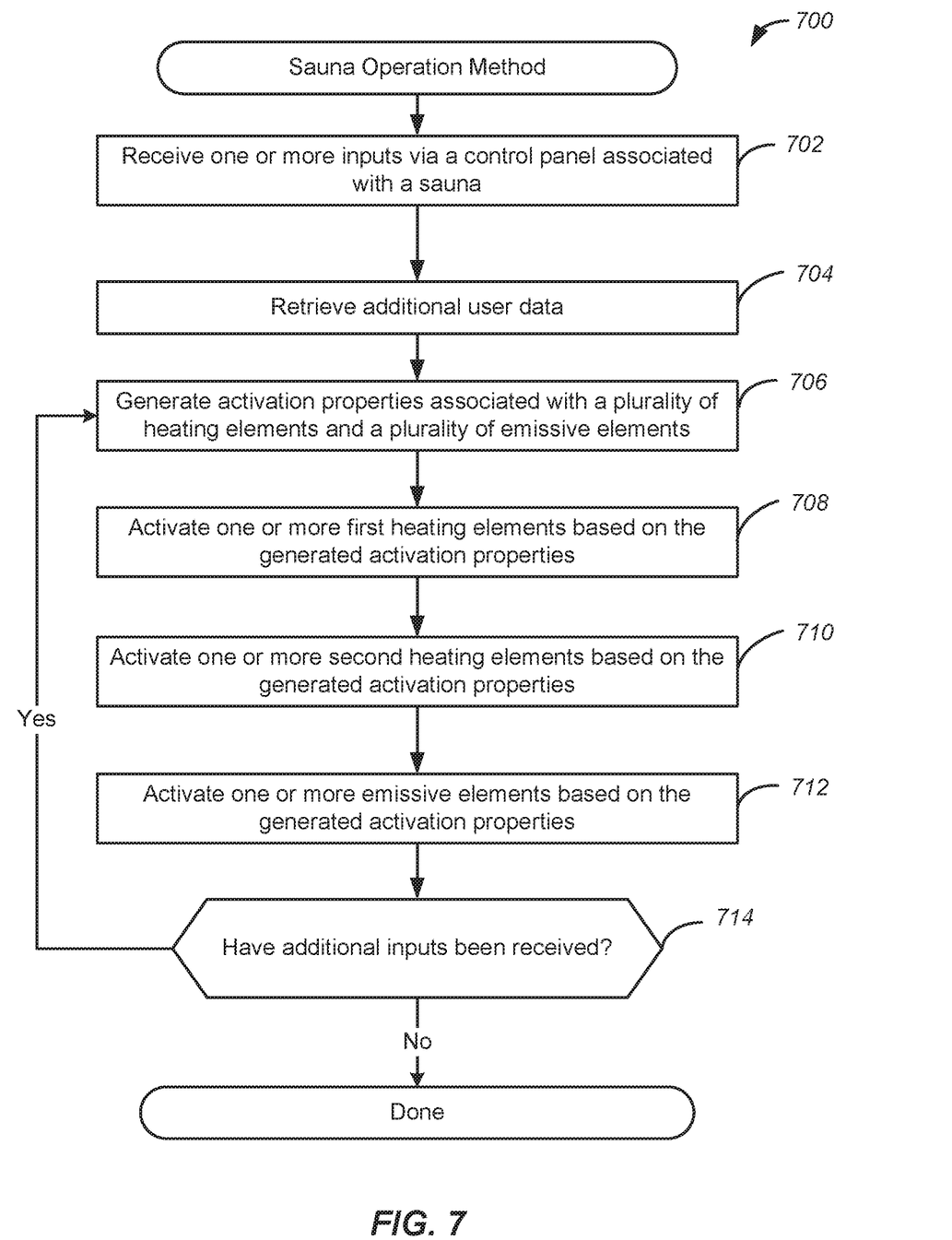
FIG. 7 illustrates a flow chart of another example of a method for controlling a sauna, implemented in accordance with some embodiments.

FIG. 7 illustrates a flow chart of another example of a method for controlling a sauna, implemented in accordance with some embodiments. As discussed above, one or more characteristics or criteria may be used by a controller to control the operation of various heating elements and emissive elements included in the sauna. The control of the heating elements and emissive elements is implemented based on user characteristics and features retrieved from a variety of sources. Moreover, the operation of the heating elements and emissive elements and implementation of activation properties may be modified dynamically to further improve the efficacy of the implementation of activation properties by a sauna.

Method 700 may commence with operation 702 during which one or more inputs may be received. In various embodiments, the inputs are received from the user via buttons included in a control panel of a controller. In some embodiments, the input provided by the user initiates a therapeutic session, and causes the sauna to start. In some embodiments, the inputs may also identify one or more characteristics of the user. For example, one or more prompts may be provided to the user via a display included in the control panel. The prompts may ask the user for particular information, such as known skin conditions or other health concerns. Such responses may be stored in a memory as user data.

Method 700 may proceed to operation 704 during which additional user data may be retrieved. As stated above, user data may be stored in a user profile locally in a memory of the sauna. In various embodiments, additional user data may also be stored locally, or may be stored remotely in a remote storage system that is communicatively coupled with the sauna. The additional user data may include additional information characterizes additional features or characteristics of the user. For example, the additional user data may identify the user's age, gender, weight, and skin color or complexion. The additional user data may also include other characteristics, such as occupation. In various embodiments, such other characteristics may be used to approximate an estimated daily exposure to sunlight, which may be used to adjust or modify activation parameters as will be discussed in greater detail below. In various embodiments, the additional user data may be retrieved from one or more other user profiles, such a social network account or other online service.

Method 700 may proceed to operation 706 during which during which activation properties associated with heating elements and emissive elements may be generated. As discussed above with reference to FIG. 6, the activation properties may determine times/durations and intensities of the activation and deactivation of heating elements and emissive elements. In this way, such activation properties characterize when each individual heating element and emissive element is active and inactive over a given period of time. More specifically, activation properties characterize a particular on/off cycle for each heating element and each emissive element, as well as an intensity for each on cycle. Accordingly, the activation properties identify when each heating element and each emissive element is on or off and with what intensity over a given period of time. As discussed in greater detail below, such parameters are determined based, at least in part, on the previously identified characteristics.

In various embodiments, the activation properties are determined and generated based on combinations of one or more received and identified characteristics. For example, a user's height, weight, and skin complexion may be used to identify a particular duration and intensity of activation of the emissive elements. In one example, such characteristics may be used to identify a particular number of international units (IUs) of vitamin D over a period of time (such as per day), and the activation properties, such as intensity and duration, of the emissive elements may be configured to promote the generation of the determined number of IUs by the user during the period of time defined by the current therapeutic session. In this example, the activation properties may be further configured based on the height of the emissive element as well as an estimate of its distance from the user. Moreover, an identified condition such as psoriasis, might be used to identify an estimation of an intensity and duration of activation of heating elements. Furthermore, other factors, such as an identified occupation or ambient conditions and ambient sunlight may be used to modify or weight the activation properties.

Method 700 may proceed to operation 708 during which one or more first heating elements is activated based on the activation properties. Accordingly, the controller may activate one or more heating elements based on the previously generated activation properties. As similarly discussed above, the activation properties may identify times and intensities of activation for each of the first heating elements. In various embodiments, the first heating elements may be those mounted at torso-level within the sauna, such as heating elements 110 and 112 discussed above.

Method 700 may proceed to operation 710 during which one or more second heating elements is activated based on the activation properties. As similarly discussed above, the controller may activate one or more heating elements based on the previously generated activation properties, and the activation properties may identify times and intensities of activation for each of the second heating elements. In various embodiments, the second heating elements may be those mounted at calf-level within the sauna, such as heating elements 104 discussed above. In this way, heating elements corresponding to different parts or regions of the user's body are operated independently and may be configured to concurrently address multiple therapeutic issues in different areas associated with the user.

Method 700 may proceed to operation 712 during which one or more emissive elements is activated based on the activation properties. As similarly discussed above, the controller may activate one or more emissive elements based on the previously generated activation properties, and the activation properties may identify times and intensities of activation for each of the emissive elements. As also discussed above, the activation may be for a designated period of time at a designated intensity that may be determined, at least in part, on characteristics of the user, and a vitamin D requirement of the user. In this way, a particular amount of narrowband UV radiation may be provided to the user in a manner that is specifically configured based on the user's needs, and in conjunction with heat therapy provided by the heating elements.

Method 700 may proceed to operation 714 during which it may be determined if an additional input has been received. The additional input may be received from the user via the control panel, or may be received from a sensor. In various embodiments, the additional input indicates that one or more changes should be made to the activation properties. For example, the input may be received from the user and may indicate that heat therapy should be stopped. In another example, the input may be received from an internal sensor and may indicate that sufficient narrowband UV radiation has been generated, or that ambient conditions have changed. If it is determined that an additional input has been received, method 700 may return to operation 706. If it is determined that no additional input has been received, method 700 may terminate.

Figure 8:
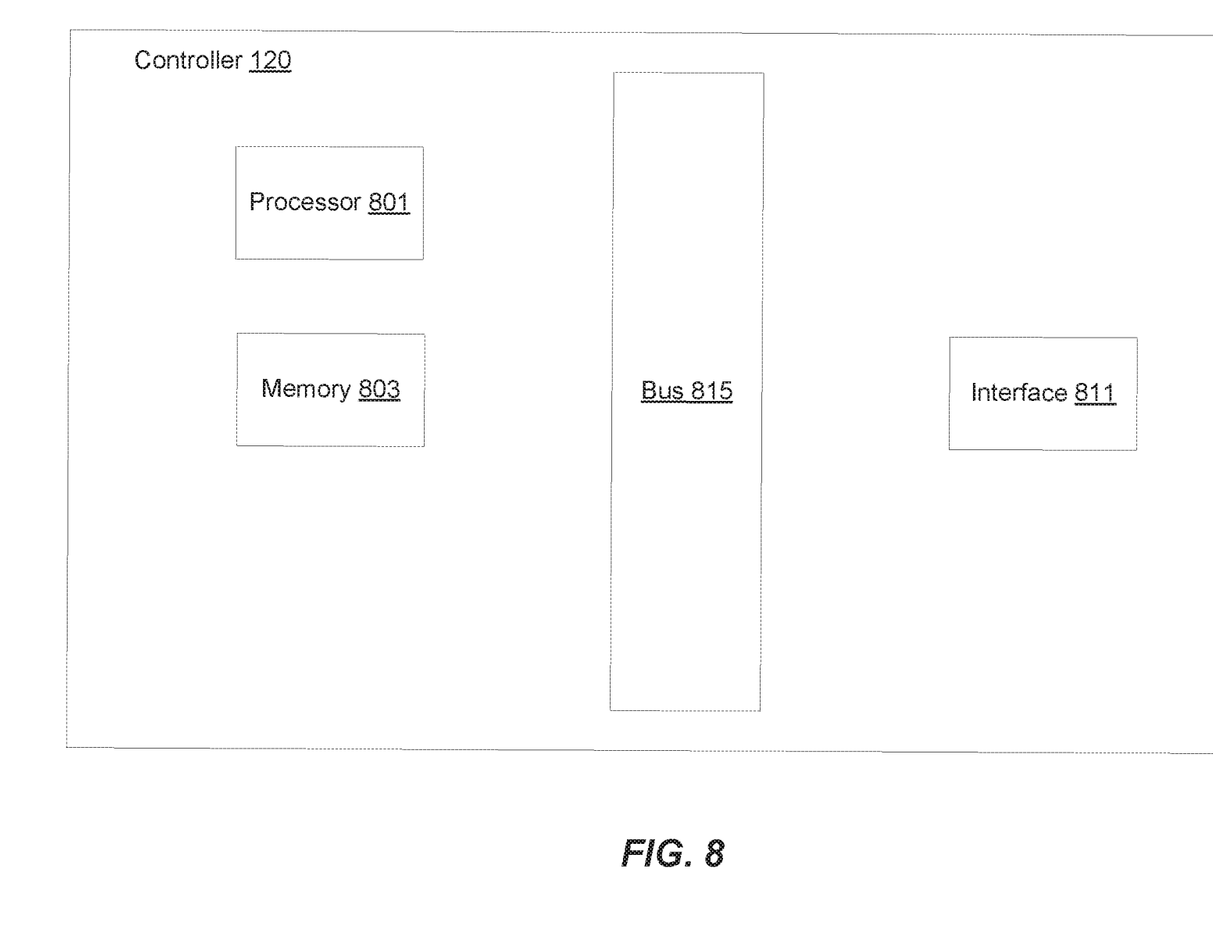
FIG. 8 illustrates one example of a controller, configured in accordance with some embodiments.

FIG. 8 illustrates one example of a controller, configured in accordance with some embodiments. According to particular embodiments, a system 800 suitable for implementing particular embodiments of the present invention includes a processor 801, a memory 803, an interface 811, and a bus 815 (e.g., a PCI bus or other interconnection fabric) and operates as a controller, such as controller 120, configured to control the operation of control panels, as discussed above. When acting under the control of appropriate software or firmware, the processor 801 is responsible for receiving inputs and controlling the operation of heating elements. In some embodiments, system 800 may be integrated in controller 120 discussed above, or may be implemented separately as a stand-alone component that provides functionalities for controller 120. Various specially configured devices can also be used in place of a processor 801 or in addition to processor 801. The interface 811 is typically configured to send and receive data. In some embodiments, such an interface may be configured to send packets or data segments over a network.

Particular examples of interfaces supported include Ethernet interfaces, cable interfaces, DSL interfaces, token ring interfaces, and the like. In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate system components. In some cases, they may also include an independent processor and, in some instances, volatile RAM. The independent processors may control communications-intensive tasks.

According to various embodiments, the system 800 is a controller configured to control the operation of heating elements in accordance with the modes and operations discussed above. For example, the system 800 may be configured to control heating elements as shown in FIG. 1. The controller may include one or more hardware elements as shown in FIG. 8. In some implementations, one or more of the controller components may be virtualized. For example, a physical server may be configured in a localized or cloud environment. Although a particular controller is described, it should be recognized that a variety of alternative configurations are possible. For example, the modules may be implemented on another device connected to a server.

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. A system comprising:
a plurality of walls of an enclosure, the enclosure being a sauna enclosure configured to accommodate a user;
a plurality of heating elements coupled to the plurality of walls;
a plurality of emissive elements configured to generate narrowband ultraviolet (UV) radiation;
a power coupler coupled to the plurality of emissive elements, wherein the plurality of emissive elements is removably coupled to a door of the sauna via a mount on the door, and wherein the power coupler is coupled to the plurality of emissive elements via a power cable;
a sensor configured to detect when sufficient narrowband UV radiation has been generated;
a controller coupled to the plurality of heating elements, and coupled to the plurality of emissive elements, the controller comprising one or more processors configured to:
identify a duration and intensity of activation and deactivation during a designated period of time for each of the plurality of heating elements and each of the plurality of emissive elements;
activate at least one of the plurality of heating elements based on the identified durations and intensities; and
activate at least one of the plurality of emissive elements based on the identified durations and intensities and based on an enabling of the power coupler by the controller; and
a memory communicatively coupled to the one or more processors and configured to store one or more data values representing the identified durations and intensities.

2. The system of claim 1, wherein the identified durations and intensities are determined based, at least in part, on a plurality of characteristics of the user.

3. The system of claim 2, wherein the characteristics of the user comprise:
one or more identified health conditions of the user; and
one or more identified vitamin D requirements of the user.

4. The system of claim 3, wherein the duration and intensity of the activation of at least one of the plurality of emissive elements is determined based on the one or more identified vitamin D requirements of the user.

5. The system of claim 1, wherein the plurality of heating elements comprises:
a first plurality of heating elements configured to provide heat to a first portion of the user; and
a second plurality of heating elements configured to provide heat to a second portion of the user.

6. The system of claim 1, wherein the first and second plurality of heating elements comprises infrared heating elements are configured to generate at least one of near infrared, mid infrared, and far infrared wavelengths.

7. The system of claim 1, wherein the first infrared heating element emits near infrared wavelengths and the second infrared heating element emits far infrared wavelengths.

8. The system of claim 1 further comprising:
a seat configured to enable the user to sit in a seated position within the enclosure, wherein the seat comprises an additional plurality of heating elements, and wherein the controller is further configured to control operation of the additional plurality of heating elements.

9. A system comprising:
a plurality of walls of an enclosure, the enclosure being a sauna enclosure configured to accommodate a user;
a plurality of heating elements coupled to the plurality of walls, the plurality of heating elements configured to generate heat;
at least one emissive element configured to generate narrowband ultraviolet (UV) radiation;
a power coupler coupled to the at least one emissive element, wherein the at least one emissive element is removably coupled to a door of the sauna via a mount on the door, and wherein the power coupler is coupled to the at least one emissive element via a power cable;
a sensor configured to detect when sufficient narrowband UV radiation has been generated;
a controller comprising one or more processors configured to control operation of the plurality of heating elements and the at least one emissive element, the one or more processors of the controller being configured to identify a duration and intensity of activation and deactivation during a designated period of time for each of the plurality of heating elements and the at least one emissive element, and wherein the one or more processors of the controller are configured to enable and disable the power coupler to control activation of the at least one emissive element; and
a memory communicatively coupled to the one or more processors and configured to store one or more data values representing the identified durations and intensities.

10. The system of claim 9, wherein the plurality of heating elements comprises:
a first plurality of heating elements configured to provide heat to a first portion of the user; and
a second plurality of heating elements configured to provide heat to a second portion of the user.

11. The system of claim 9, wherein the first and second plurality of heating elements comprises infrared heating elements are configured to generate at least one of near infrared, mid infrared, and far infrared wavelengths.

12. The system of claim 9, wherein the identified durations and intensities are determined based, at least in part, on a plurality of characteristics of the user.

13. The system of claim 9 further comprising:
a seat configured to enable the user to sit in a seated position within the enclosure, wherein the seat comprises an additional plurality of heating elements, and wherein the controller is further configured to control operation of the additional plurality of heating elements.

* * * * *